United States Patent [19]

Levinthal

[11] Patent Number: 4,785,094
[45] Date of Patent: Nov. 15, 1988

[54] CRYSTALLIZATION OF BETA HMX

[75] Inventor: Michael L. Levinthal, Marshall, Tex.

[73] Assignee: Morton Thiokol, Inc., Chicago, Ill.

[21] Appl. No.: 912,437

[22] Filed: Sep. 26, 1986

[51] Int. Cl.[4] .......................................... C07D 257/02
[52] U.S. Cl. .................................................... 540/475
[58] Field of Search ........................................ 540/475

[56] References Cited

U.S. PATENT DOCUMENTS

| | | | |
|---|---|---|---|
| 3,069,477 | 12/1962 | Lee et al. | 260/644 |
| 3,297,681 | 1/1967 | Wright et al. | 540/475 |
| 3,304,300 | 2/1967 | Watters | 540/475 |
| 3,676,425 | 7/1972 | Dawson et al. | 540/475 |
| 3,770,721 | 11/1973 | Robbins et al. | 540/475 |
| 4,086,228 | 4/1978 | Solomon et al. | 540/475 |
| 4,432,902 | 2/1984 | McGuire et al. | 540/475 |

FOREIGN PATENT DOCUMENTS 1228616 11/1966 Fed. Rep. of Germany .
1463470 12/1966 France .

OTHER PUBLICATIONS

Bachmann et al., CA 46: 2084d to 2085a.
Kodak, CA67(16): 75044j.
Lee et al., CA 58a: 5448g.
Siele et al., "Alternative Processes for HMX Manufacture", Technical Report ARLCD-T5-78008 (Oct. 1979).

Primary Examiner—Richard L. Raymond
Assistant Examiner—D. B. Springer
Attorney, Agent, or Firm—George Wheeler; Gerald K. White

[57] ABSTRACT

Method of directly precipitating substantially pure beta HMX from a substantially anhydrous nitric acid solution without forming and recrystallizing polymorphic HMX. HMX dissolved in a solvent consisting essentially of anhydrous nitric acid is added to water which is seeded with crystals of beta HMX to substantially completely precipitate all the HMX from solution as beta HMX without forming crystals of the other polymorphic forms of HMX. A preferred reaction and apparatus for preparing HMX in anhydrous nitric acid is also disclosed.

7 Claims, 1 Drawing Sheet

CRYSTALLIZATION OF BETA HMX

TECHNICAL FIELD

The present invention relates to manufacture of crystalline octahydro-1,3,5,7-tetranitro-1,3,5,7-tetrazine, alternatively known as cyclotetramethylenetetranitramine; 1,3,5,7-tetranitro-1,3,5,7-tetraazacyclooctane; homocyclonite; octagen; or by Chemical Abstracts Registry No. 2691-41-0. The common name of this material is HMX; it is a high explosive which is primarily useful for military applications. Its structure is:

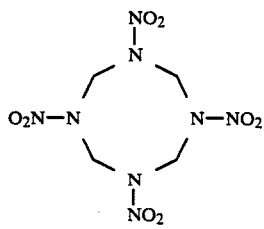

BACKGROUND ART

HMX is a crystalline solid used as an explosive and as an ingredient of propellants. It is polymorphic, having four crystalline forms commonly knonw as alpha HMX, beta HMX, gamma HMX, and delta HMX. Beta HMX is considered to be the least impact sensitive of the four, and for that reason is the only form of HMX which meets present military specifications. For reasons of safety and efficiency, it would be desirable to crystallize HMX in the beta form exclusively.

U.S. Pat. No. 4,432,902, issued to McGuire, et al. on Feb. 21, 1984, teaches the formation of HMX by addition of dinitrogen pentoxide ($N_2O_5$) to a solution of 1,5-diacetyl-3,7-dinitro-1,3,5,7-tetraazacyclooctane (DADN):

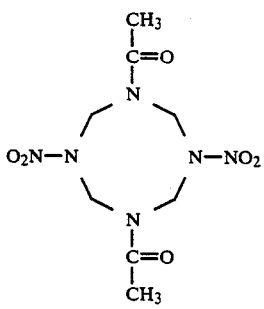

or 1,3,5,7-tetraazacyclooctane (TAT) in an unspecified solvent (which is understood to be anhydrous nitric acid) to form a solution of HMX. The solution is then poured into a bath of water (in which HMX is insoluble) to cause the HMX to crystallize. While the McGuire patent uses the reaction scheme preferred herein, beta HMX is not consistently produced because the reaction conditions, particularly at the point where the HMX solution is added to water, are not precisely controlled. McGuire discloses that a concentrated acid should be added to water suddenly (Example 14) to precipitate HMX. This causes localized or general exotherms which encourage formation of undesired polymorphs of HMX. McGuire's method has been shown to be difficult to practice on a larger than laboratory scale.

An earlier example of prior art is U.S. Pat. No. 3,297,681, issued to Wright, et al. on Jan. 10, 1967. This patent describes a process for producing beta HMX. In the Wright process, crude (polymorphic) HMX is first produced in crystalline form. This step in itself is dangerous, for polymorphic or impure HMX is less stable than pure beta HMX. The crude HMX is then dissolved in an organic solvent, the solution is cooled to supersaturate it, seeded with critically sized beta HMX, and then water is added to the HMX solution suddenly to precipitate HMX. The solvent is then removed and the residue filtered to extract beta HMX. The Wright, et al. process will produce beta HMX, but the intermediate production of crude HMX is hazardous, and should be avoided. Also, the Wright, et al. process requires that the HMX in solution must be saturated before it can be seeded, since the seed crystals would dissolve in an unsaturated solution. The process thus is not useful for recrystallizing HMX from more dilute solutions. This process also suffers from the need to precisely control process conditions so that beta HMX will be quantitatively formed to the exclusion of the other polymorphs.

Several other pertinent references are U.S. Pat. Nos. 3,304,300, issued to Watters on Feb. 14, 1967; 3,676,425, issued to Dawson, et al. on July 11, 1972; 3,770,721 issued to Robbins, et al. on Nov. 6, 1973; and 4,086,228, issued to Solomon, et al. on Apr. 25, 1978; and French Pat. No. 1,463,470, issued Dec. 23, 1966, cited in *Chemical Abstracts*, Vol. 67 (16) 75044j.

OBJECTS OF THE INVENTION

A first object of the present invention is to prepare substantially pure beta HMX without intermediate crystallization of crude HMX containing impurities or other polymorphic forms. A second object of the invention is to provide a process for producing beta HMX which is as efficient as possible, desirably eliminating energy intensive recrystallizing, concentrating, and other operations. A third object of the invention is to produce beta HMX by a process which is more easily controlled and has less narrowly defined critical parameters than prior art processes. A fourth object of the invention is to provide a process in which the exothermic reaction between nitric acid and water during the quenching step is carefully controlled. Other objects of the invention will become apparent from the description which follows.

SUMMARY OF THE INVENTION

The invention is an improved method for selectively producing crystalline beta HMX, comprising the steps of providing a solution of HMX in nitric acid, providing water seeded with beta HMX seed crystals, and mixing these two components by adding the HMX solution to the seeded water, thereby selectively precipitating beta HXM.

In the preferred practice of the present invention, the solution of HMX in nitric acid is the unisolated reaction product of DADN with dinitrogen pentoxide in anhydrous nitric acid. By using this reaction product in situ as the medium from which beta HMX is directly crystallized, the previously known steps of crystallizing crude HMX from the nitric acid solution, dissolving it in a second solvent, and recrystallizing pure beta HMX from the second solvent are eliminated. Also, the media from which beta HMX is crystallized or recrystallized do not need to be saturated with HMX to avoid dissolving the seed crystals.

BRIEF DESCRIPTION OF DRAWING

The FIGURE is a schematic view of the apparatus used to practice the preferred mode of the invention.

The reference characters used herein are as follows:
10: reactor
12: DADN supply vessel
14: $N_2O_5$/$HNO_3$ supply vessel
16: jacket (of 14)
18: jacket (of 10)
20: line
22: valve
24: line
26: pump
28: line
30: valve
32: line
34: heat exchanger
36: line
38: line
40: line
42: line
44: emergency dump tank
46: valve
48: line
50: source of seeded $H_2O$
52: quench tank
54: jacket (of 52)
56: line
58: pump
60: valve
62: line
68: heat exchanger
70: line
72: valve
74: line
76: static mixer
78: line
80: valve
82: line
84: valve
86: line
88: line
90: valve
92: line
94: filter
96: arrow
98: line
100: valve
102: neutralizer
104: line
106: line
108: line
110: line
112: line.

DESCRIPTION OF THE PREFERRED EMBODIMENT

Figure 1:
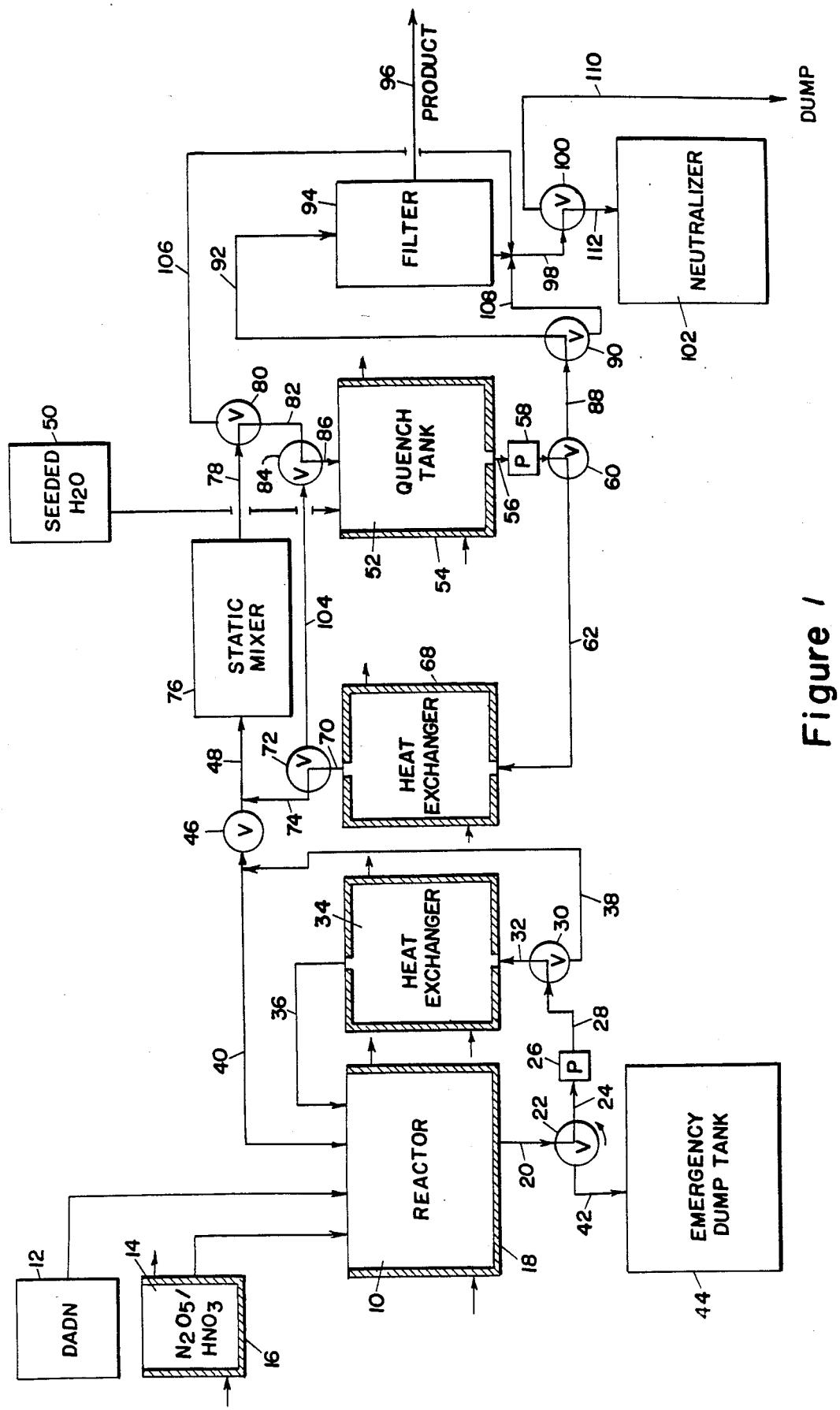

The present process involves the reaction of DADN with dinitrogen pentoxide to form HMX in nitric acid solution, followed by a second reaction in which HMX is precipitated by combining the nitric acid solution with water seeded with beta HMX crystals, and in which the acetyl nitrate side product of the first reaction is reacted with water to form acetic acid and additional nitric acid. The reactions can be set forth as follows:

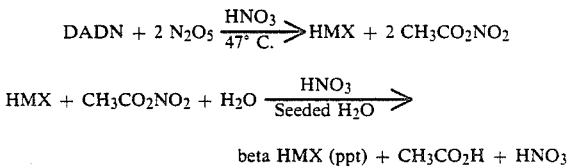

Referring to the FIGURE, the first reaction set forth immediately above takes place in reactor 10. DADN, which is a solid, is delivered from a supply vessel 12 which includes a screw feeder (not shown). The dinitrogen pentoxide and nitric acid solvent are stored in a jacketed supply vessel 14, the jacket 16 of which is fed by brine at 30° to 40° C. to keep the mixture at 40° C. or less. For each mole of DADN fed to reactor 10, from about 2–4 moles, preferably about 3.8 moles of dinitrogen pentoxide (the stoichiometric amount would be 2 moles) and about 26 moles of anhydrous nitric acid are added. Reactor 10 contains stirring means (not shown) to uniformly disperse the ingredients and products and to provide even heat transfer. Reactor 10 is also provided with a jacket 18 which is fed with heated water to maintain the mixture in reactor 10 at about 47° C. during the reaction. The temperature of the reaction is preferably controlled between 45° and 55° C. If the material in reactor 10 becomes too hot during the reaction, it can be pumped via line 20 to a valve 22 and line 24 by pump 26, then through line 28, valve 30, line 32, heat exchanger 34 and line 36 to return the reaction mixture to reactor 10. Alternatively, the contents of reactor 10 can be circulated without heat exchange by switching valve 30 so it connects lines 28 and 38 and disconnects line 32 from communication. In this instance the flow is through line 20, valve 22, line 24, pump 26, line 28, valve 30, line 38, and line 40. In the event the mixture within reactor 10 is in danger of excessive exotherm, whether due to excessive heat or formation of unstable forms of HMX, valve 22 can be reversed to place lines 20 and 42 in communication, thereby quickly draining the contents of reactor 10 into emergency dump tank 44 which is a stirred vessel, partially filled with water, having enough additional capacity to contain the contents of reactor 10.

When the contents of reactor 10 have fully reacted, and thus contain HMX and acetyl nitrate dissolved in anhydrous nitric acid, valve 30 is reversed as explained above to provide communication beteen lines 28 and 38, and valve 46 is opened to pass the product mixture to line 48. Meanwhile, for each mole of the original DADN about 20 moles of deionized water are charged to quench tank 52 and seeded with about 0.5% by weight of 3.2 micron weight mean diameter (WMD) seeds of beta HMX provided from source 50. Quench tank 52 is provided with stirring means (not shown) and a jacket 54 for circulating brine to provide cooling. The initial contents of quench tank 52 are thus pure seeded water. Quench tank 52 is provided with a first recycle and mixing loop comprising line 56, pump 58, valve 60, line 62, heat exchanger 68, line 70, valve 72, line 74, line 48, static mixer 76, line 78, valve 80, line 82, valve 84, and line 86. When valves 60, 72, 80 and 84 are in the positions illustrated in the FIGURE, the contents of quench tank 52 are cooled in heat exchanger 68, mixed in line 48 and static mixer 76 with the reaction product passing through valve 46, and returned to quench tank 52. Thus, in this system water is diluted by adding acid, instead of the reverse. Another consequence of this particular system is that the HMX passing through valve 46 is immediately contacted with a relatively large volume of water, thus insuring the immediate and total precipitation of beta HMX from solution. When the entire reaction product from reactor 10 and associated lines has passed through valve 46 and has been combined with seeded water, thus carrying out the second reaction set forth earlier in this description, valve 60 is reversed to bring the outlet of pump 58 into communication with line 88 and out of communication with line 62. The contents of the quench tank are thus pumped through line 88, valve 90, and line 92 to filter 94 from which a pure beta HMX filter cake is removed (represented by arrow 96). The filtrate comprising the solvents and liquid products of reaction is passed via line 98 and valve 100 to a neutralizer 102.

In the preferred embodiment, if the contents of quenck tank 52 exceed 55° C., valve 60 is reversed to transmit the contents of quench tank 52 to filter 94. It is unsafe to maintain the contents of quench tank 52 at a greater temperature, as the acetyl nitrate intermediate product can detonate if this temperature is substantially exceeded.

Valve 22 is shifted only in an emergency to terminate the first stage reaction precipitously in the event of danger. Valves 72 and 84 are operated in tandem, and are reversed from the illustrated position to connect lines 70, 104, and 86 and disconnect lines 74 and 82. The result is to directly connect heat exchanger 68 with quench tank 52 and to terminate the mixing of the product of the first stage with the seeded water. This can be done to interrupt the quenching step without wasting any of the reaction mixture if the temperature in the quench tank recycle loop exceeds a desirable value. Valve 80 can be reversed to connect line 78 with line 106 and to disconnect line 82. This precaution would be taken to drain the contents of line 48, static mixer 76, and line 78 in the event of overheating in those parts of the system. Valve 90 can be reversed to connect line 88 to line 108 and to disconnect line 92. This can be done should filter 94 become clogged and the temperature in quench tank 52 exceed a safe level, or alternatively, this can be used in conjunction with reversal of valve 60 to drain quench tank 52 quickly in the event of an unsafe condition. Valve 100 can be reversed to connect line 98 with line 110 and to disconnect line 112 feeding neutralizer 102 in the event it is necessary to more quickly damp material from lines 98, 106, or 108, or if neutralizer 102 becomes overloaded.

In the above process, the weight ratio of the nitric acid solvent to the water nonsolvent is from about 90:10 to about 40:60 and the nitric acid solution passing through valve 46 comprises from about 5% to about 20% by weight HMX. The desirable concentration of HMX seed crystals in the water originally provided from source 50 depends on the size (WMD) of the seed crystals, but is preferably from about 0.1% to about 1% by weight, most preferably about 0.5% by weight. The seed crystals have a weight mean diameter between about 1 and about 50 microns. It is preferred that the first stage reaction product passing through valve 46 and the seeded water (and later other reactants) passing through line 74 be provided at from abut 30° to about 50° C.

In the preferred practice of the process, the reaction mixture upstream of valve 46 and downstream of the reactant feeds contains no more than about 30% dinitrogen pentoxide, no more than about 4% dinitrogen tetroxide, no more than about 5.5% by weight acetyl nitrate, and no more then about 1% by-products of formation of HMX by weight. There is substantially no water in the system upstream of valve 46. Downstream of that valve, once the first stage reaction product is fully charged through valve 46 and completely mixed with the contents of quench tank 52, the resulting final mixture contains no more than about 30% by weight of water.

The present process can also be practiced apart from the illustrated system, as described in the following example.

EXAMPLE I

10% by weight of dry HMX was dissolved in anhydrous nitric acid at a temperature of 47° C. Separately, 90 ml. of deionized water were placed in a 500 ml beaker in an ice bath and 0.5% by weight of 3.2 micron (WMD) seeds of beta HMX were dispersed in the water. The beaker was equipped with a magnetic stirring bar to maintain the dispersion.

The solution of HMX in nitric acid was then added dropwise to the water dispersion in the beaker. As each drop contacted the water, it turned milk white, indicating precipitation of HMX. When addition was complete the dispersion was filtered through a Buchner funnel having a ½ micron pore size. The filtrate was drawn through the funnel using laboratory vacuum. The filter cake was removed and dried in a vacuum oven overnight at about 60° C., then weighed. About 80% of the original HMX was recovered. The dried crystals were examined under a microscope, and crystals of beta HMX were found. No crystals of the other polymorphic forms were present.

This example illustrates that pure beta HMX can be directly recrystallized from a predominantly nitric acid solution according to the present process to produce substantially pure beta HMX which is essentially free of the other polymorphic forms.

I claim:

1. A method for selectively producing crystalline beta HMX, comprising the steps of:
    A. providing an unsaturated solution of HMX in a solvent consisting essentially of nitric acid;
    B. providing a dispersion of beta HMX seed crystals in a nonsolvent consisting essentially of water; and
    C. adding said solution of HMX to said dispersion, thereby precipitating beta HMX selectively from said solution of HMX.

2. The method of claim 1, wherein said solution of HMX comprises from about 5 to about 20% by weight HMX.

3. The method of claim 1, wherein the weight ratio of said solvent to said nonsolvent is from about 90:10 to about 40:60.

4. The method of claim 1, wherein the concentration of said crystals in said nonsolvent is from about 0.1% to about 1% by weight.

5. The method of claim 4, wherein said concentration is about 0.5% by weight.

6. The method of claim 1, wherein said seed crystals have a weight mean diameter between about 1 and 50 microns.

7. The method of claim 1, further comprising the subsequent step of separating said precipitated beta HMX from the mixture of said solvent and said nonsolvent.

* * * * *